(12) United States Patent
Juan et al.

(10) Patent No.: US 11,779,325 B2
(45) Date of Patent: Oct. 10, 2023

(54) KNOT DELIVERY DEVICE

(71) Applicant: Terumo Medical Corporation, Somerset, NJ (US)

(72) Inventors: Chun-Chia Juan, Taipei (TW); William Aldrich, Taipei (TW); Yu-Shih Weng, Taipei (TW)

(73) Assignee: Terumo Medical Corporation, Somerset, NJ (US)

(*) Notice: Subject to any disclaimer, the term of this patent is extended or adjusted under 35 U.S.C. 154(b) by 86 days.

(21) Appl. No.: 16/954,903

(22) PCT Filed: Dec. 18, 2018

(86) PCT No.: PCT/US2018/066210
§ 371 (c)(1),
(2) Date: Jun. 17, 2020

(87) PCT Pub. No.: WO2019/126152
PCT Pub. Date: Jun. 27, 2019

(65) Prior Publication Data
US 2020/0390437 A1 Dec. 17, 2020

Related U.S. Application Data

(60) Provisional application No. 62/607,218, filed on Dec. 18, 2017.

(51) Int. Cl.
*A61B 17/04* (2006.01)
*A61B 90/00* (2016.01)
*A61B 17/00* (2006.01)

(52) U.S. Cl.
CPC ............ *A61B 17/0469* (2013.01); *A61B 2017/00004* (2013.01); *A61B 2017/00358* (2013.01);
(Continued)

(58) Field of Classification Search
CPC ......... A61B 17/0469; A61B 2090/064; A61B 2090/0807; A61B 2017/00358; A61B 2017/0474; A61B 2017/0477
See application file for complete search history.

(56) References Cited

U.S. PATENT DOCUMENTS 5,312,423 A    5/1994  Rosenbluth et al.
5,330,491 A *  7/1994  Walker ............... A61B 17/0469
                                                606/139
(Continued)

FOREIGN PATENT DOCUMENTS

JP    2012-520141 A    9/2012
JP    2014-523764 A    9/2014
(Continued)

OTHER PUBLICATIONS

Extended European Search Report from corresponding European Patent Application No. 18891122.6, dated Aug. 9, 2021.
(Continued)

*Primary Examiner* — Tan-Uyen T Ho
*Assistant Examiner* — David P Stein
(74) *Attorney, Agent, or Firm* — Dergosits & Noah LLP; Todd A. Noah

(57) ABSTRACT

A knot delivery device for securing a suture comprises an elongated body having a proximal end and a distal end, a pre-configured knot disposed at the distal end of the elongated body, a suture snare having a snare configured to capture suture material, wherein the snare extends through the pre-configured knot and a suture locker secured to one end of material forming the pre-configured knot, wherein tension applied to the suture locker tightens the pre-configured knot.

18 Claims, 7 Drawing Sheets

(52) U.S. Cl.
CPC ............... *A61B 2017/0474* (2013.01); *A61B 2017/0477* (2013.01); *A61B 2090/064* (2016.02); *A61B 2090/0807* (2016.02)

(56) References Cited

U.S. PATENT DOCUMENTS

| | | | |
|---|---|---|---|
| 5,562,688 | A | 10/1996 | Riza |
| 5,591,177 | A | 1/1997 | Lehrer |
| 5,797,928 | A * | 8/1998 | Kogasaka ........ A61B 17/12009 |
| | | | 606/139 |
| 5,814,052 | A | 9/1998 | Nakao et al. |
| 5,817,107 | A | 10/1998 | Schaller |
| 8,608,758 | B2 | 12/2013 | Singhatat et al. |
| 11,026,690 | B2 | 6/2021 | Fung et al. |
| 11,219,446 | B2 * | 1/2022 | Bonutti ............ A61B 17/1675 |
| 2010/0249809 | A1 | 9/2010 | Singhatat et al. |
| 2011/0245850 | A1 | 10/2011 | Van Den Burg et al. |
| 2014/0236188 | A1 * | 8/2014 | Mehl ................. A61B 17/0469 |
| | | | 606/144 |
| 2016/0183937 | A1 | 6/2016 | Miraki et al. |
| 2018/0103947 | A1 * | 4/2018 | Nobles |

FOREIGN PATENT DOCUMENTS

| | | |
|---|---|---|
| JP | 2016086980 A | 5/2016 |
| WO | 2017070312 A1 | 4/2017 |

OTHER PUBLICATIONS

International Search Report and Written Opinion from International Patent Application No. PCT/US2018/066210, dated Mar. 14, 2019.
Notification of Reasons for Refusal in corresponding Japanese Patent Application No. 2020-533619, dated Nov. 29, 2022.
Notice of Preliminary Rejection from corresponding Korean Patent Application No. 10-2020-7020502 dated May 25, 2023.

* cited by examiner

KNOT DELIVERY DEVICE

RELATED APPLICATIONS

This application claims priority to and the benefit of U.S. Provisional Patent Application Ser. No. 62/607,218, filed Dec. 18, 2017, the contents of which is incorporated in its entirety herein by reference.

FIELD OF THE PRESENT DISCLOSURE

The present disclosure relates generally to devices and methods for delivering a pre-configured knot to cinch or tighten suture material that has been previously deployed. In particular, techniques are disclosed for delivering a pre-configured knot from an external location to a percutaneous location, such as to secure a suture to help close a wound.

BACKGROUND

Techniques have been developed to allow an increasing number and variety of procedures to be performed percutaneously, as minimally invasive alternatives to conventional "open" surgeries that provide the benefits of reducing post-operative pain, decreasing hospital stays and periods of disability, and lowering costs for both hospitals and patients. Generally, these procedures utilize one or more elongated instruments that are introduced through a patient's skin for use in carrying out the procedure. For example, access to the patient's vasculature may be obtained by creating an opening in a suitable artery or vein.

However, in order to accommodate the instruments used during a percutaneous procedure, the openings may have relatively large diameters. A variety of methods may be used to close the access opening. Conventionally, hemostasis may be achieved through manual compression to substantially reduce the flow of blood through the opening and allow clot formation. Although generally successful, compression may take a significant amount of time and may be associated with considerable patient discomfort. Additionally, complications such as unintended total occlusion of the lumen that may result in ischemia or thrombosis can occur. These aspects may be exacerbated depending upon the size of the opening necessary to introduce the percutaneous device, whether anticoagulants are employed and on the condition of the patient.

Correspondingly, it is desirable to attempt repair or otherwise provide support for the surrounding tissue during the post-operative healing process. Closing openings formed to carry out a percutaneous procedure with sutures may reduce recovery time, minimize the risk of infection or provide other benefits. Although other methods of closing wounds have been developed, such as using staples and clips, suturing remains a reliable technique that provides advantages over these alternatives. Conventionally, a sliding suture knot is formed in a suture loop has been tied by a procedure operator manually outside the port used to access the patient's body. Then, the knot may be advanced distally until adjacent the blood vessel by a suitable device, i.e. knot pusher, so as to help close the opening of the blood vessel. However, tying the knot typically requires a high level of surgical skill to produce reliable and reproducible knots in the suture loop necessary to ensure the efficiency and safety of hemostasis. Therefore, there is a need for techniques that improve knot tying efficiency and reproducibility to achieve hemostasis. As will be described in the materials below, the devices and methods of this disclosure satisfy these and other needs.

SUMMARY

This disclosure includes a knot delivery device for securing a suture having an elongated body with proximal and distal ends, a pre-configured knot disposed at the distal end of the elongated body, a suture snare having a snare configured to capture suture material, wherein the snare extends through the pre-configured knot and a suture locker secured to one end of material forming the pre-configured knot, wherein tension applied to the suture locker tightens the pre-configured knot.

In one aspect, the suture snare may be detachably secured to the elongated body.

In one aspect, the suture locker may be detachably secured to the elongated body.

In one aspect, the snare and the material forming the pre-configured knot may extend through at least one lumen having an opening at the distal end of the elongated member. Further, the snare and the material forming the pre-configured knot may each extend separate lumens having openings at the distal end of the elongated member. The opening may be sized to allow passage of the material forming the pre-configured knot but not a pattern of turns of the pre-configured knot.

In one aspect, proximal movement of the suture snare may be configured to pull the snare through the pre-configured knot.

In one aspect, proximal movement of the suture locker may be configured to tighten the pre-configured knot.

In one aspect, the suture locker may include a force indicator. The force indicator may employ a spring having a biasing force, wherein a tension sufficient to tighten the pre-configured knot is configured to overcome the biasing force. The force indicator may have a visual marking configured to indicated when a tension sufficient to tighten the pre-configured knot has been applied to the suture locker. Alternatively, the force indicator may have a frangible element secured to the material forming the pre-configured knot.

In one aspect, the material forming the pre-configured knot may include a rail limb and a non-rail limb, wherein the rail limb may be secured to the suture locker. As such, the snare may extend through at least one helical turn of the non-rail limb around the rail limb.

This disclosure also includes a method for delivering a pre-configured knot for securing a suture. The method may involve providing a knot delivery device having an elongated body with a proximal end and a distal end, wherein the pre-configured knot is disposed at the distal end of the elongated body, a suture snare, wherein the snare extends through the pre-configured knot, and a suture locker secured to one end of material forming the pre-configured knot, capturing suture material with the snare, withdrawing the snare to pull the captured suture material through the pre-configured knot, tightening the pre-configured knot around the suture material and advancing the pre-configured knot over the suture material to a desired location.

In one aspect, withdrawing the snare may involve detaching the suture snare from the elongated body.

In one aspect, tightening the pre-configured knot may involve detaching the suture locker from the elongated body.

In one aspect, tightening the pre-configured knot may involve applying tension to the suture locker until sufficient force has been indicated. The indication of sufficient force may be visual. Alternatively, the indication of sufficient force may involve breakage of a component of the suture locker.

BRIEF DESCRIPTION OF THE DRAWINGS

Further features and advantages will become apparent from the following and more particular description of the preferred embodiments of the disclosure, as illustrated in the accompanying drawings, and in which like referenced characters generally refer to the same parts or elements throughout the views, and in which.

DETAILED DESCRIPTION

At the outset, it is to be understood that this disclosure is not limited to particularly exemplified materials, architectures, routines, methods or structures as such may vary. Thus, although a number of such options, similar or equivalent to those described herein, can be used in the practice or embodiments of this disclosure, the preferred materials and methods are described herein.

It is also to be understood that the terminology used herein is for the purpose of describing particular embodiments of this disclosure only and is not intended to be limiting.

The detailed description set forth below in connection with the appended drawings is intended as a description of exemplary embodiments of the present disclosure and is not intended to represent the only exemplary embodiments in which the present disclosure can be practiced. The term "exemplary" used throughout this description means "serving as an example, instance, or illustration," and should not necessarily be construed as preferred or advantageous over other exemplary embodiments. The detailed description includes specific details for the purpose of providing a thorough understanding of the exemplary embodiments of the specification. It will be apparent to those skilled in the art that the exemplary embodiments of the specification may be practiced without these specific details. In some instances, well known structures and devices are shown in block diagram form in order to avoid obscuring the novelty of the exemplary embodiments presented herein.

For purposes of convenience and clarity only, directional terms, such as top, bottom, left, right, up, down, over, above, below, beneath, rear, back, and front, may be used with respect to the accompanying drawings. These and similar directional terms should not be construed to limit the scope of the disclosure in any manner.

Unless defined otherwise, all technical and scientific terms used herein have the same meaning as commonly understood by one having ordinary skill in the art to which the disclosure pertains. Notably, aspects of this disclosure are described in the context of a cardiovascular procedure.

Finally, as used in this specification and the appended claims, the singular forms "a, "an" and "the" include plural referents unless the content clearly dictates otherwise.

Figure 1A:
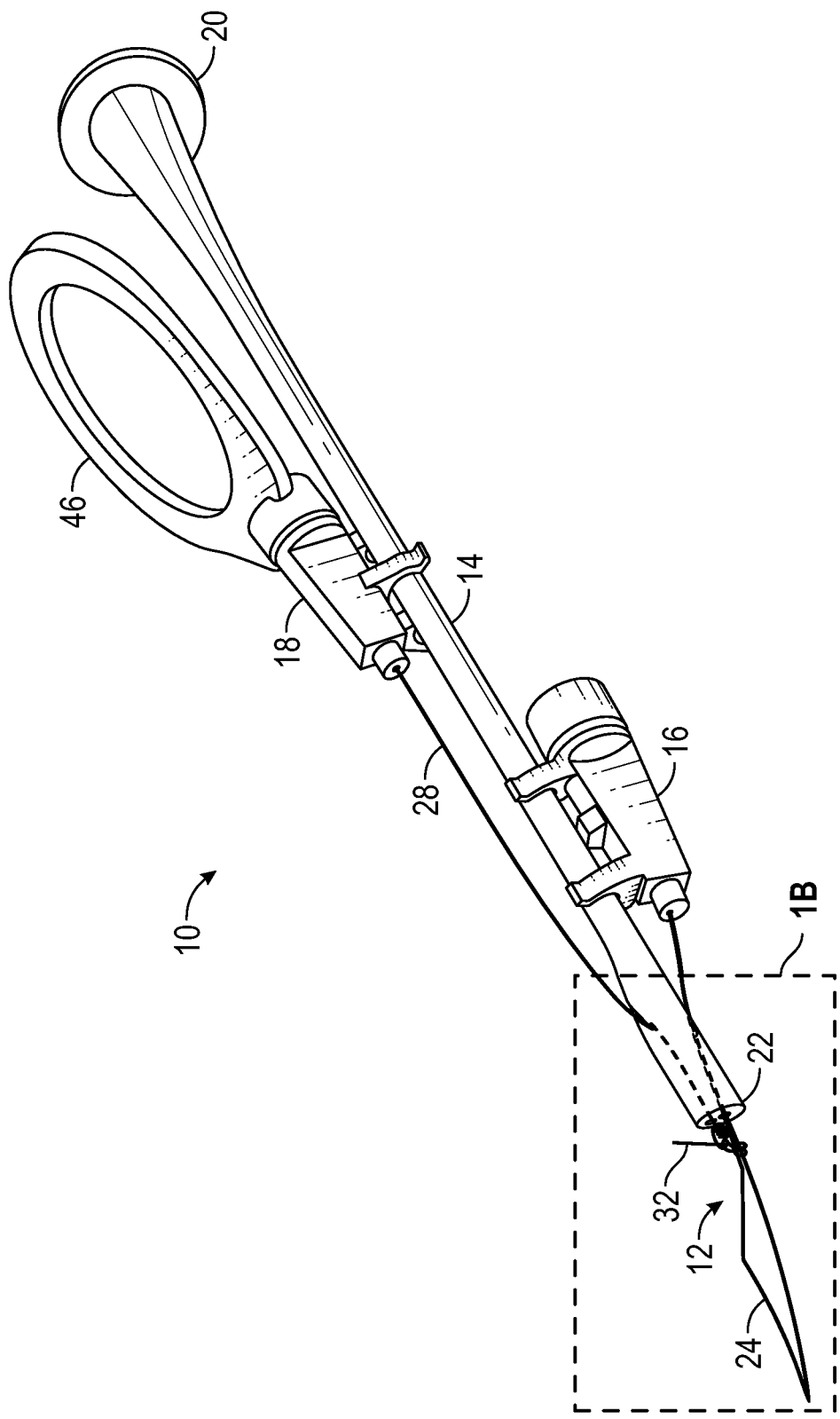
FIG. 1A depicts a schematic view of an embodiment of a knot delivery device, according to an embodiment of this disclosure.
Figure 1B:
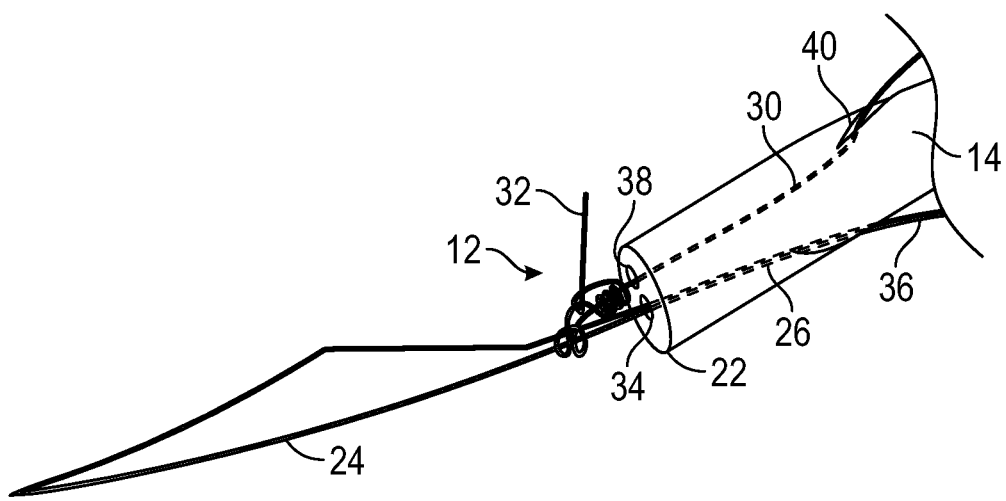
FIG. 1B depicts a schematic enlarged view of a snare and a pre-configured knot of the knot delivery device in FIG. 1A.

Referring to FIG. 1A and the detailed view of FIG. 1B, a knot delivery device 10 according to one embodiment is shown. The knot delivery device 10 is configured to percutaneously deliver a pre-configured knot 12 from an external location to a desired location within a patient over suture material (not shown in this view) to secure the suture material and facilitate wound closure. As depicted, knot delivery device 10 for securing or locking a suture closure includes an elongated body 14, a suture snare 16 and a suture locker 18, wherein suture snare 16 and suture locker 18 may respectively be detachably coupled or secured to elongated body 14. The elongated body 14 has a proximal end 20 and a distal end 22. The suture snare 16 has a snare 24 formed by a loop of flexible material configured to be disposed over and capture the suture material, with the opposing ends routed through a lumen 26 at distal end 22 of elongated body 14 and secured to suture snare 16. Suture locker 18 has pre-configured knot 12 disposed at distal end 22 of elongated body 14, with at least one end, such as rail limb 28 routed through a lumen 30 at distal end 22 of elongated body 14 and secured to suture locker 18. As will be described in further detail below, pre-configured knot 12 may be formed by a pattern of multiple turns of non-rail limb 32 around rail limb 28. Pre-configured knot 12 and snare 24, as well as the suture material itself, may each be synthetic or natural, such as a polymer, gut, metallic wire or other suitable equivalents. Each of the materials may be substantially the same, or one or more may be different in order to exhibit characteristics tailored to their respective functions. For example, the material for pre-configured knot 12 may have a relatively greater surface friction to facilitate cinching and securing the knot about the suture material. As another non-limiting illustration, either or both the materials used for the suture and pre-configured knot 12 may be biodegradable or bio-absorbable. Similarly, the respective materials may be of substantially the same gauge or thickness or may differ as desired. Snare 24 of suture snare 16 extends through pre-configured knot 12 so that once the suture material is captured by snare 24, withdrawing suture snare 16 causes the suture material to be pulled though pre-configured knot 12. In turn, pre-configured knot 12 may then be advanced over the suture material and cinched tight to secure the suture material and facilitate wound closure as described in the materials below.

In the present embodiment, lumen 26 and lumen 30 may be separate and communicate between distal end 22 of elongated body 14 and lateral positions that are distal of where suture snare 16 and suture locker 18 are detachably secured to form pathways for the material of snare 24 and pre-configured knot 12, respectively. For example, both ends of snare 24 are shown in FIG. 1B as extending through lumen 26, which communicates between opening 34 at distal end 22 of elongated body 14 and lateral port 36. Similarly, at least one end of the material forming pre-configured knot 12, such as rail limb 28, extends through lumen 30, which communicates between opening 38 at distal end 22 of elongated body 14 and lateral port 40.

Notably, opening 38 may be sized to allow passage of rail limb 28 but not the pattern of pre-configured knot 12 formed by the turns of non-rail limb 32. As such, withdrawing rail limb 28 causes the helical turns of non-rail limb 32 to abut distal end 22, and because they cannot enter opening 38, the turns of non-rail limb 32 constrict around rail limb 28, cinching and tightening the knot by friction. It will be appreciated that in other embodiments, a single lumen may be used, with the material of pre-configured knot 12 and snare 24 extending through the same pathway. However, it may be desirable to employ two lumens as shown in order to reduce the chance of entanglement between the components.

Returning to the overall view of knot delivery device 10 shown in FIG. 1A, suture snare 16 may be secured to elongated body 14. In some embodiments, suture snare 16 is detachably secured, such as through clips 42 (not shown in FIG. 1A) that extend partially around elongated body 14. As noted above, the opposing ends of the material forming snare 24 are in turn secured to suture snare 16. Correspondingly, after the suture material has been captured by extending through the loop of snare 24, suture snare 16 may be detached from elongated body 14 to facilitate withdrawing the material of snare 24 to pull the captured suture material through pre-configured knot 12. Alternatively, suture snare 16 need not be detachable and the operator may grasp the material of snare 24 directly to affect the withdrawal. Similarly, it may also be seen that suture locker 18 may also be detachable from elongated body 14, such as by clip 44 (not shown FIG. 1A). Since at least one end of the material forming pre-configured knot 12 is secured to suture locker 18, detachment of suture locker 18 conveniently allows rail limb 28 to be pulled in a proximal direction, causing pre-configured knot 12 to abut distal end 22 of elongated body 14 and be cinched tight as discussed above. Further, suture locker 18 may also comprise pull tab 46 that is coupled to the end of the pre-configured knot 12 material that extends through lumen 30. As will be described in further detail below, the attachment between pull tab 46 and pre-configured knot 12 may be designed to facilitate applying sufficient tension to cinch pre-configured knot 12 appropriately tight without over-tightening. In other embodiments, if desired, suture locker 18 need not be detachable and the operator may directly grasp rail limb 28 when cinching the knot.

As noted above, pre-configured knot 12 may be formed by making an appropriate pattern of helical turns of non-rail limb 32 around rail limb 28 as indicated in FIG. 1B. According to this disclosure, pre-configured knot 12 may be any sliding knot, such as a fisherman's knot, a clinch knot or an improved clinch knot, as well as any other knot known in clinical practices. In one aspect, pre-configured knot 12 may be formed around snare 24 or the knot may be formed first, and snare 24 then passed through an appropriate location. For example, snare 24 extends through at least one of the turns of non-rail limb 32. One end of the material forming pre-configured knot 12, such as rail limb 28, enters lumen 30 through opening 38 in distal end 22 of elongated body 14 and then exits through lateral port 40 before being coupled to suture locker 18 as described above.

Figure 2:
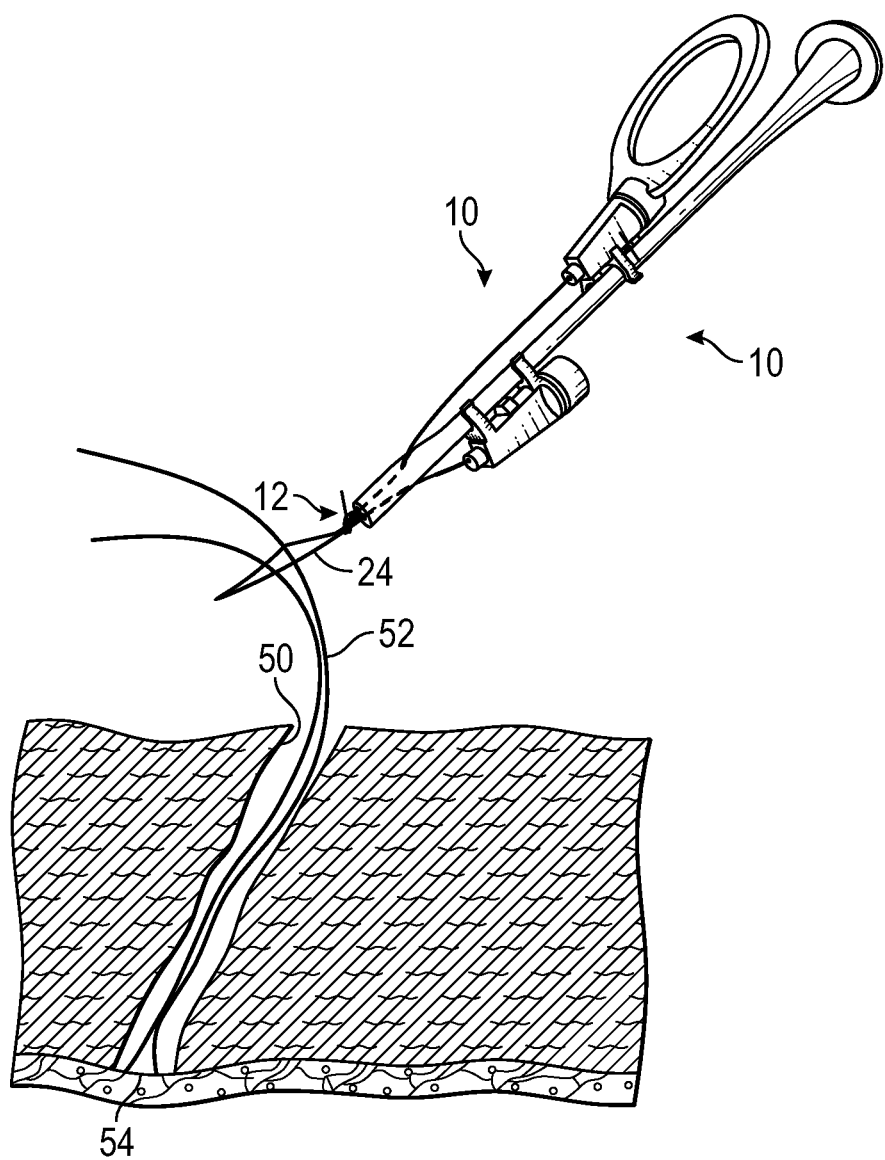
FIG. 2 depicts a schematic view of two strands of suture material passed through the snare of knot delivery device in FIG. 1A.
Figure 3A:
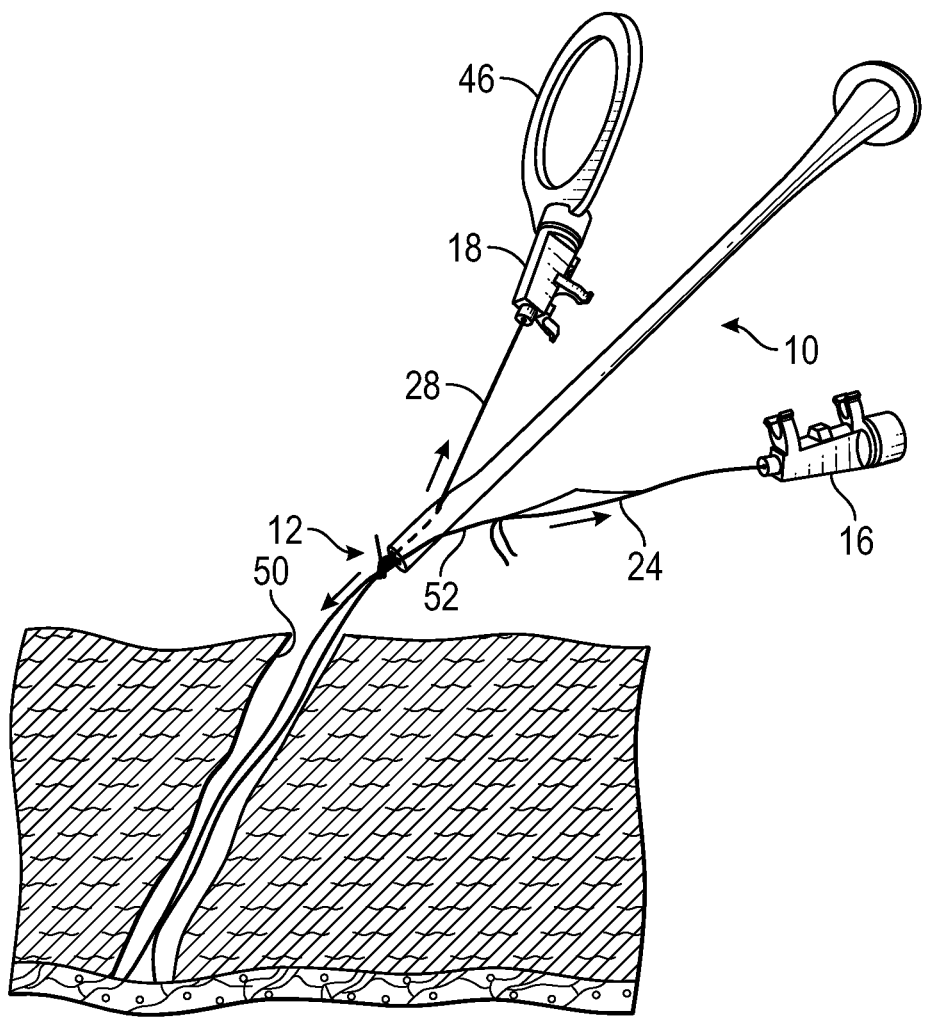
FIGS. 3A-3B schematically depict a sequence of operations in delivering external pre-configured knot to add onto suture material with an embodiment of knot delivery device, according to an embodiment of this disclosure.
Figure 3B:
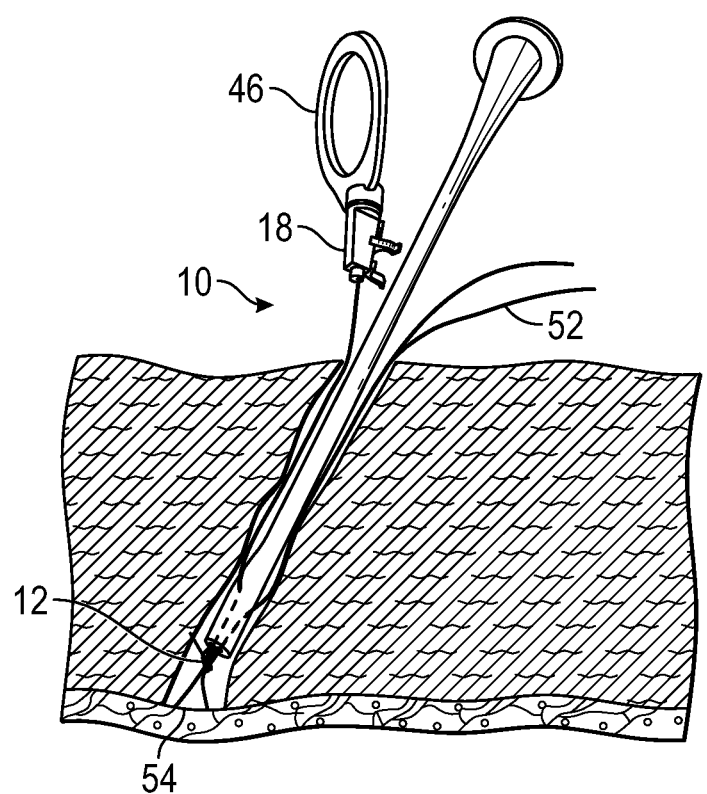

An exemplary usage of knot delivery device 10 is schematically depicted in FIGS. 2-3. For example, beginning with FIG. 2, a tissue track 50 has been created to provide access to a percutaneous location within the patient. One common location is a portion of the patient's vasculature, such as a vessel like the femoral artery. However, the techniques of this disclosure are not limited to any specific location and may be used to deliver a knot over suture material in any suitable application. Following creation of tissue track 50 and performance of a procedure involving one or more medical devices accessing the percutaneous location, the device(s) are withdrawn and it would be desirable to help close and support the wound as discussed above. Therefore, suture material 52 may be threaded through tissue track 50 and engage tissue at the wound site 54. Any suitable technique for placing suture material 52 may be employed, including manually or through the use of suture delivery devices, including those disclosed in co-pending, commonly-owned U.S. patent application Ser. Nos. 14/726,963 and 14/726,996, both of which are incorporated by reference in their entirety. As shown in FIG. 2, suture material 52 may comprise two free ends, such that cinching a knot adjacent to where the suture engages the patient's tissue will secure the suture. However, the techniques of this disclosure may be applied to secure any number of strands of suture material as desired. As indicated by FIG. 2, snare 24 may be used to capture the free ends of suture material 52 by passing them through the loop of snare 24. Then, as schematically shown in FIG. 3A, suture snare 16 may be detached from elongated body 14 and withdrawn proximally to pull snare 24 through pre-configured knot 12 and then through lumen 26. Since snare 24 has captured the free ends of suture material 52, the suture material is also pulled through pre-configured knot 12 and lumen 26. Once suture material 52 has been pulled through pre-configured knot 12, suture locker 18 may be detached from elongated body 14 and proximal pre-tension applied to pre-configured knot 12 (via rail limb 28 for example) to be compacted by manipulating pull tab 46. After sufficient pre-tension has been applied to cinch pre-configured knot 12 around suture material 52, elongated body 14 may then be advanced through tissue track 50 to slide pre-configured knot 12 along suture material 52 until it is adjacent location 54 where the suture material engages the patient's tissue to secure the suture and help close the wound as schematically indicated in FIG. 3B. Depending on the embodiment, cinching pre-configured knot 12 may be performed in one operation, before the pre-tensioned knot is advanced to its final location to secure the suture, i.e., applying an initial tension before advancing the knot and then applying a final tension once the knot is in its desired location.

Figure 4:
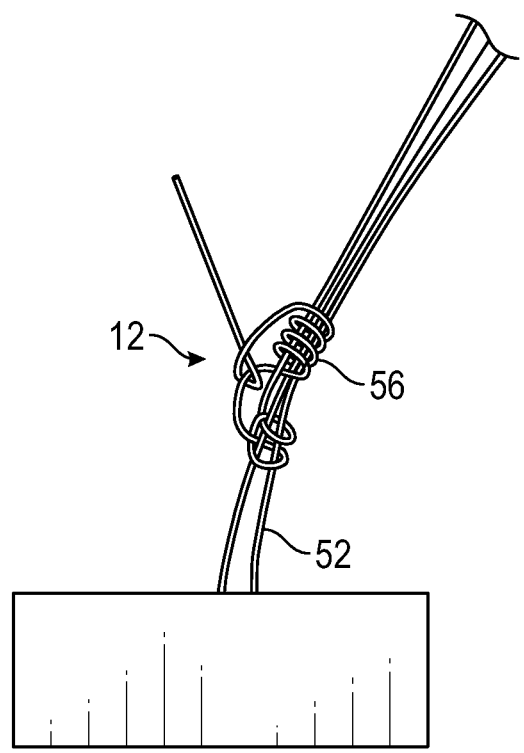
FIGS. 4-5 depict schematic views of configurations of pre-configured knot, according to an embodiment of this disclosure.
Figure 5:
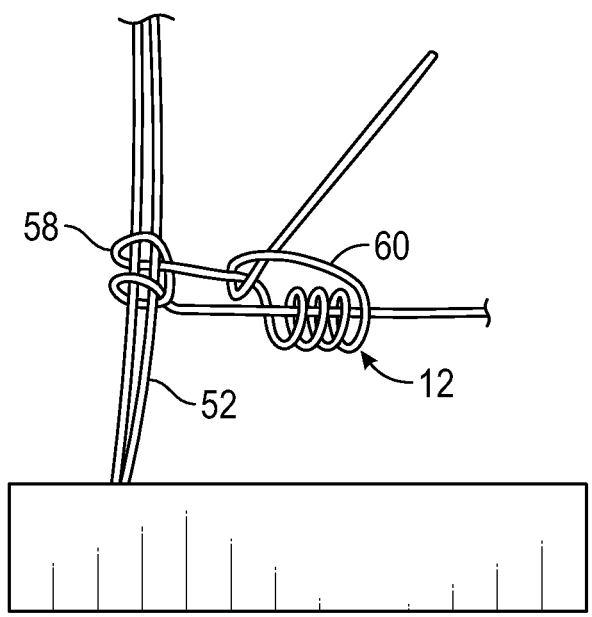

As noted above, pre-configured knot 12 may be tied using any suitable pattern that allows it to be slid along and tightened around the suture material to secure a suture. As one non-limiting illustration, pre-configured knot 12 may employ a fisherman's knot pattern 56 as shown in FIG. 4. Alternatively, pre-configured knot 12 may further include at least one suture loop 58 adjacent to a fisherman knot pattern 60 as shown in FIG. 5. Suture loop 58 may be configured to cinch suture material 52 for securing it. In some embodiments, the addition of suture loop 58 adjacent to fisherman's knot pattern 60 in pre-configured knot 12 may increase the locking force applied to suture material 52. As shown, suture loop 58 may be a reverse loop, but other configurations may be employed as desired.

Figure 6A:
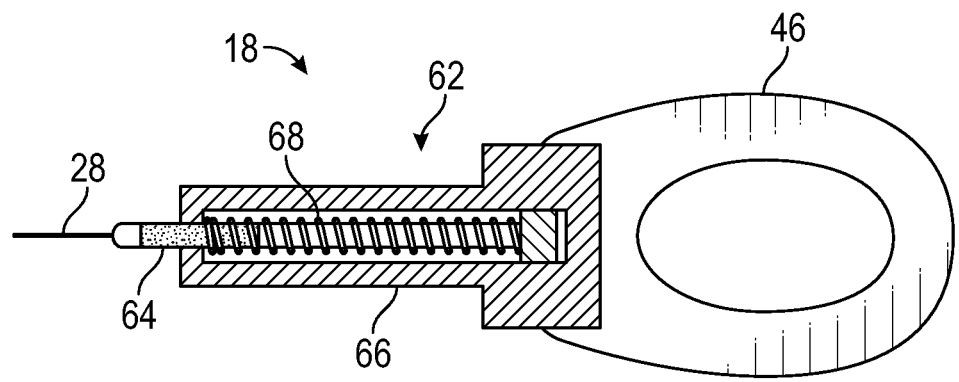
FIGS. 6A-6B depict schematic views of a force indicator, according to an embodiment of this disclosure.
Figure 6B:
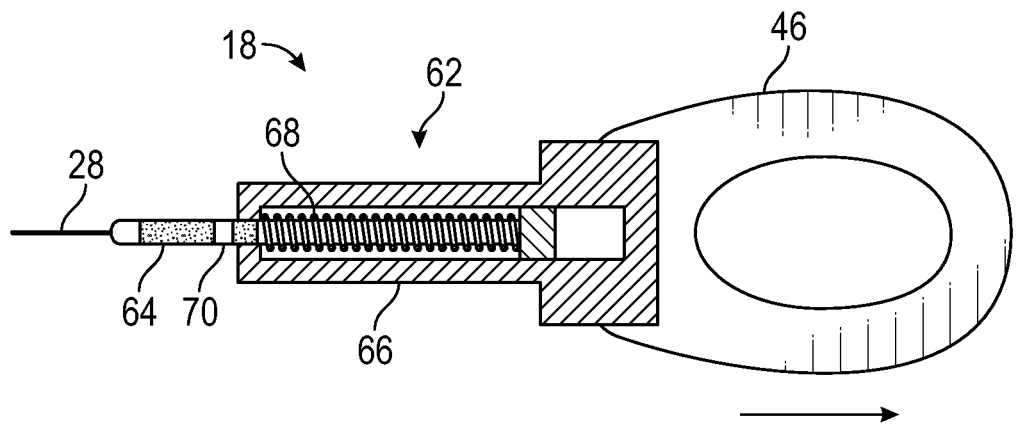
Figure 7:
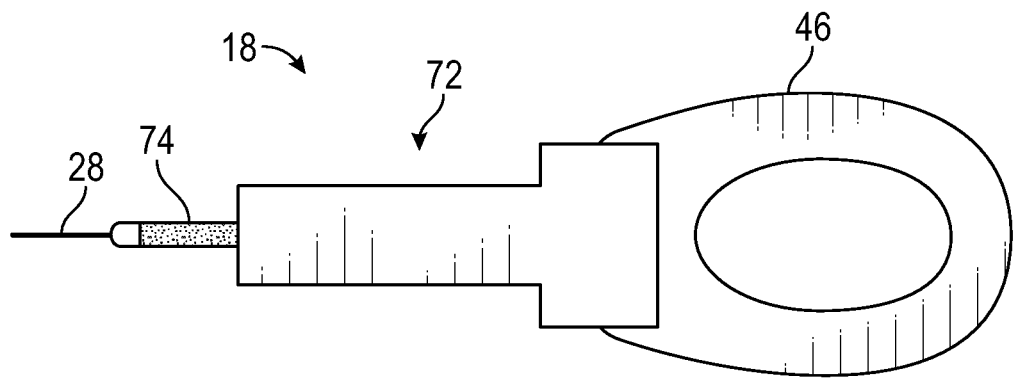
FIG. 7 depicts a schematic view of a force indicator having a frangible element, according to an embodiment of this disclosure.

In some embodiments, the attachment between pull tab 46 and pre-configured knot 12 may be designed to facilitate applying sufficient tension to cinch pre-configured knot 12 appropriately tight without over-tightening as discussed above. For example, FIGS. 6A and 6B schematically depict pull tab 46 that features force indicator 62 to facilitate the application of a given amount of tension when tightening pre-configured knot 12. Rail limb 28 may be secured to piston 64 that is disposed within housing 66 secured to pull tab 46. Compression spring 68 is coaxially disposed over piston 64 and biases it in a proximal direction, with the native configuration shown in FIG. 6A. Correspondingly, when sufficient proximal tension is applied to pull tab 46 to overcome the biasing force of spring 68, piston 64 travels distally relative to housing 66 as shown in FIG. 6B. In one embodiment, a visual marking 70 may be provided along this range of travel in order to indicate when a desired amount of tension has been applied. In this embodiment, marking 70 emerges from housing 66 and becomes visible when sufficient tension has been applied, but any other type of visual indication may be employed. Alternatively or in addition, force indicator 62 may provide a tactile indication, such as when spring 68 begins to compress or when piston 64 reaches the end of its range of travel within housing 66. It will be appreciated that these embodiments are intended to be illustrative and should not be considered limiting. Any suitable mechanism for indicating the tension that is applied to pre-configured knot 12 may be used as known in the art. Again, for the purpose of illustration, another embodiment is shown in FIG. 7. Force indicator 72 secures rail limb 28 to pull tab 46 through frangible element 74. Frangible element 74 may be formed from a polymer or other material having a calibrated strength that breaks when the desired tension has been applied.

As will be appreciated from the material above, knot delivery device 10 employs pre-configured knot 12 and advances it from an external location to a percutaneous location to secure suture material and facilitate closure of a wound or medical procedure access site. Correspondingly, the techniques of this disclosure avoid the complications and difficulties associated with tying a suture knot manually in the desired location. Further, the use of pre-configured knots allows them to be formed in a reproducible manner, such as automatically during manufacture, and overcomes variability that may exist when using conventional knot-tying practices. Still further, the use of knot delivery device 10 to deliver pre-configured knots 12 may substantially reduce the time necessary to appropriately secure sutures used for closing wounds or other purposes.

Described herein are certain exemplary embodiments. However, one skilled in the art as it pertains to the present embodiments will understand that the principles of this disclosure can be extended easily with appropriate modifications to other applications.

What is claimed is:

1. A knot delivery device for securing a suture, comprising:
    an elongated body having a proximal end and a distal end;
    a pre-configured knot disposed at the distal end of the elongated body;
    a suture snare having a snare formed by a loop of flexible material configured to be disposed over and capture suture material, the suture snare having opposing ends routed through a lumen at the distal end of the elongated body, wherein the snare extends through the pre-configured knot; and
    a suture locker secured to one end of material forming the pre-configured knot, wherein tension applied to the suture locker tightens the pre-configured knot.

2. The knot delivery device of claim 1, wherein the suture snare is detachably secured to the elongated body.

3. The knot delivery device of claim 1, wherein the suture locker is detachably secured to the elongated body.

4. The knot delivery device of claim 1, wherein the snare and the material forming the pre-configured knot extend through at least one lumen having an opening at the distal end of the elongated body.

5. The knot delivery device of claim 4, wherein the snare and the material forming the pre-configured knot each extend separate lumens having openings at the distal end of the elongated body.

6. The knot delivery device of claim 4, wherein the opening is sized to allow passage of the material forming the pre-configured knot but not a pattern of turns of the pre-configured knot.

7. The knot delivery device of claim 1, wherein proximal movement of the suture snare is configured to pull the snare through the pre-configured knot.

8. The knot delivery device of claim 1, wherein proximal movement of the suture locker is configured to tighten the pre-configured knot.

9. The knot delivery device of claim 1, wherein the suture locker comprises a force indicator.

10. The knot delivery device of claim 9, wherein the force indicator comprises a spring having a biasing force, wherein a tension sufficient to tighten the pre-configured knot is configured to overcome the biasing force.

11. The knot delivery device of claim 9, wherein the force indicator comprises a visual marking configured to indicated when a tension sufficient to tighten the pre-configured knot has been applied to the suture locker.

12. The knot delivery device of claim 9, wherein the force indicator comprises a frangible element secured to the material forming the pre-configured knot.

13. The knot delivery device of claim 1, wherein the material forming the pre-configured knot comprises a rail limb and a non-rail limb, wherein the rail limb is secured to the suture locker.

14. The knot delivery device of claim 13, wherein the snare extends through at least one helical turn of the non-rail limb around the rail limb.

15. A method for delivering a pre-configured knot for securing a suture, comprising:
    providing a knot delivery device having an elongated body with a proximal end and a distal end, wherein the pre-configured knot is disposed at the distal end of the elongated body, a suture snare having a snare formed by a loop of flexible material configured to be disposed over and capture suture material, the suture snare having opposing ends routed through a lumen at the distal end of the elongated body, wherein the snare extends through the pre-configured knot, and a suture locker secured to one end of material forming the pre-configured knot;
    capturing suture material with the snare;
    withdrawing the snare to pull the captured suture material through the pre-configured knot;
    advancing the pre-configured knot over the suture material to a desired location; and
    tightening the pre-configured knot around the suture material.

16. The method of claim 15, wherein withdrawing the snare comprises detaching the suture snare from the elongated body.

17. The method of claim 15, wherein tightening the pre-configured knot comprises detaching the suture locker from the elongated body.

18. The method of claim 15, wherein tightening the pre-configured knot comprises applying tension to the suture locker until sufficient force has been indicated by one of a visual indicator or breakage of a component of the suture locker.

\* \* \* \* \*